(12) United States Patent
Shoemaker et al.

(10) Patent No.: US 10,913,709 B2
(45) Date of Patent: Feb. 9, 2021

(54) STAT3 INHIBITOR FORMULATION

(71) Applicants: The United States of America, as represented by the Secretary, Department of Health and Human Services, Bethesda, MD (US); GLG Pharma, LLC, Jupiter, FL (US); MRIGlobal, Kansas City, MO (US)

(72) Inventors: Robert H. Shoemaker, Boyds, MD (US); Michael W. Lovell, St. Johns, FL (US); Jonathan M. White, Pleasant Valley, MO (US); Shanker Gupta, Bethesda, MD (US)

(73) Assignees: The United States of America, as represented by the Secretary, Department of Health and Human Services, Bethesda, MD (US); GLG Pharma, LLC, Jupiter, FL (US); MRIGlobal, Kansas City, MO (US)

( * ) Notice: Subject to any disclaimer, the term of this patent is extended or adjusted under 35 U.S.C. 154(b) by 0 days.

(21) Appl. No.: 16/603,110

(22) PCT Filed: Apr. 5, 2018

(86) PCT No.: PCT/US2018/026228
§ 371 (c)(1),
(2) Date: Oct. 4, 2019

(87) PCT Pub. No.: WO2018/187551
PCT Pub. Date: Oct. 11, 2018

(65) Prior Publication Data
US 2020/0109109 A1 Apr. 9, 2020

Related U.S. Application Data

(60) Provisional application No. 62/481,960, filed on Apr. 5, 2017.

(51) Int. Cl.
| | | |
|---|---|---|
| C07C 309/73 | (2006.01) | |
| A61P 35/00 | (2006.01) | |
| C07C 215/10 | (2006.01) | |
| A61K 9/00 | (2006.01) | |
| A61K 9/08 | (2006.01) | |

(52) U.S. Cl.
CPC .......... C07C 309/73 (2013.01); A61K 9/0053 (2013.01); A61K 9/08 (2013.01); A61P 35/00 (2018.01); C07C 215/10 (2013.01); *C07B 2200/13* (2013.01)

(58) Field of Classification Search
CPC ..... C07C 309/73; C07C 215/10; A61P 35/00; C07B 2200/13
See application file for complete search history.

(56) References Cited

U.S. PATENT DOCUMENTS

| | | |
|---|---|---|
| 6,191,285 B1 | 2/2001 | Esser et al. |
| 7,960,434 B2 | 6/2011 | Turkson et al. |

FOREIGN PATENT DOCUMENTS

| | | |
|---|---|---|
| WO | WO 2010/062681 A2 | 6/2010 |
| WO | WO 2010/065444 A1 | 6/2010 |
| WO | WO 2012/159107 A1 | 11/2012 |

OTHER PUBLICATIONS

Ball et al., "Signal transducer and activator of transcription 3 (STAT3) inhibitor, S3I-201, acts as a potent and non-selective alkylating agent," *Oncotarget*, 7(15): 20669-20679 (2016).
Banerjee et al., "Constitutive activation of STAT3 in breast cancer cells: A Review," *Int J Cancer*, 138(11): 2570-2578 (2016).
Corvinus et al., "Persistent STAT3 Activation in Colon Cancer Is Associated with Enhanced Cell Proliferation and Tumor Growth," *Neoplasia*, 7(6): 545-555 (2005).
Dhir et al., "Stat3 Activation in Prostatic Carcinomas" *Prostate*, 51(4): 241-246 (2002).
Fletcher et al., "Antagonism of the Stat3-Stat3 Protein Dimer with Salicylic Acid Based Small Molecules," *ChemMedChem*, 6(8): 1459-1470 (2011).
Garcia et al., "Constitutive Activation of Stat3 in Fibroblasts Transformed by Diverse Oncoproteins and in Breast Carcinoma Cells," *Cell Growth & Differentiation*, 8(12): 1267-1276 (1997).
Gkouveris et al., "STAT3 Signaling in Cancer," *Journal of Cancer Therapy*, 6: 709-726 (2015).
Guo et al., "Activation of Stat3 in renal tumors," *Am J Transl Res*, 1(3): 283-290 (2009).
Huang et al., "Constitutive Activation of Stat 3 Oncogene Product in Human Ovarian Carcinoma Cells" *Gynecol Oncol*, 79(1): 67-73 (2000).
Ishii et al., "Tamoxifen Stimulates the Growth of Cyclin D1-Overexpressing Breast Cancer Cells by Promoting the Activation of Signal Transducer and Activator of Transcription 3," *Cancer Res*, 68(3): 852-860 (2008).
Marotta et al., "The JAK2/STAT3 Signaling Pathway is required for growth of CD44$^+$CD24$^-$ stem cell-Like breast cancer cells in human tumors," J Clin Invest, 121(7): 2723-2735 (2011).
Mora et al., "Constitutive Activation of Stat3 in Human Prostate Tumors and Cell Lines: Direct Inhibition of Stat3 Signaling Induces Apoptosis of Prostate Cancer Cells," *Cancer Res*, 62(22): 6659-6666 (2002).
Schaefer et al., "Constitutive activation of Stat3alpha in brain tumors: localization to tumor endothelial cells and activation by the endothelial tyrosine kinase receptor (VEGFR-2)," *Oncogene*, 21(13): 2058-2065 (2002).

(Continued)

*Primary Examiner* — Alicia L Otton
(74) *Attorney, Agent, or Firm* — Leydig, Volt & Mayer, Ltd.

(57) ABSTRACT

Disclosed is a salt prepared from the STAT3 inhibitor known as 2-hydroxy-4-[[2-[[(4-methylphenyl)sulfonyl]oxy]acetyl]amino] benzoic acid and 2-amino-2-(hydroxymethyl)-1,3-propanediol. The salt is soluble in water and stable for extended periods of time. Further provided are pharmaceutical compositions comprising the salt and methods of administering the salt to prevent and treat cancer, such as breast cancer.

16 Claims, 4 Drawing Sheets

(56) References Cited

OTHER PUBLICATIONS

Shoemaker et al., "Evaluation of the STAT3 inhibitor GLG-302 for the prevention of estrogen receptor-positive and -negative mammary cancers," *Oncology Reports*, 42(3): 1205-1213 (2019).
Watson et al., "Elevated levels of members of the STAT family of transcription factors in breast carcinoma nuclear extracts," *Br J Cancer*, 71(4): 840-844 (1995).
Wei et al., "Stat3 activation regulates the expression of vascular endothelial growth factor and human pancreatic cancer angiogenesis and metastasis," *Oncogene*, 22(3): 319-329 (2003).
Yue et al., "Targeting STAT3 in cancer: how successful are we?" *Expert Opinion Investig Drugs*, 18(1): 45-56 (2009).
European Patent Office, International Search Report in International Patent Application No. PCT/US2018/026228 (dated Jul. 4, 2018).

STAT3 INHIBITOR FORMULATION

CROSS-REFERENCE TO RELATED APPLICATIONS

This patent application is a U.S. national phase of International Patent Application No. PCT/US2018/026228, filed Apr. 5, 2018, which claims the benefit of U.S. Provisional Patent Application No. 62/481,960 filed Apr. 5, 2017, the disclosures of which are incorporated by reference for all purposes.

STATEMENT REGARDING FEDERALLY SPONSORED RESEARCH OR DEVELOPMENT

This invention was made with Government support under project number 110775.05.015.04 (A) by the National Institutes of Health, National Cancer Institute. The Government has certain rights in this invention.

BACKGROUND OF THE INVENTION

The compound 2-hydroxy-4-[[2-[[(4-methylphenyl)sulfonyl]oxy]acetyl]amino] benzoic acid (also known as 2-hydroxy-4-(2-(tosyloxy)acetamido)benzoic acid):

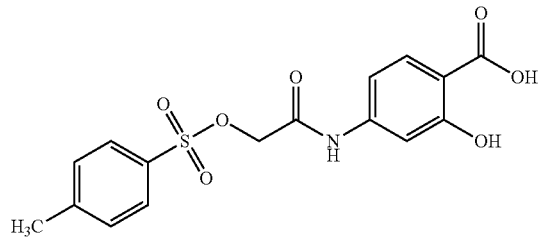 [SMILES: Cc1ccc(S(=O)(=O)OCC(=O)Nc2ccc(C(=O)O)c(O)c2)cc1]

is known in the art colloquially as NSC-74859 and S3I-201 and is a potent inhibitor of signal transducer and activator of transcription 3 (STAT3) DNA-binding activity ($IC_{50}$ of 86±33 μM in vitro). In particular, 2-hydroxy-4-[[2-[[(4-methylphenyl)sulfonyl]oxy]acetyl]amino] benzoic acid induces apoptosis in tumor cells that express activated STAT3. As a result, 2-hydroxy-4-[[2-[[(4-methylphenyl)sulfonyl]oxy]acetyl]amino] benzoic acid has been shown to be effective in treating various cancers. However, 2-hydroxy-4-[[2-[[(4-methylphenyl)sulfonyl]oxy]acetyl]amino] benzoic acid is poorly soluble in water and ethanol, so practical administration of 2-hydroxy-4-[[2-[[(4-methylphenyl)sulfonyl]oxy]acetyl]amino] benzoic acid is not readily feasible.

Thus, there remains an unmet need for improved formulations containing 2-hydroxy-4-[[2-[[(4-methylphenyl)sulfonyl]oxy]acetyl]amino] benzoic acid as an active agent to provide a method of preventing or treating cancer with improved administration and efficacy.

BRIEF SUMMARY OF THE INVENTION

The invention provides a novel salt of 2-hydroxy-4-[[2-[[(4-methylphenyl)sulfonyl]oxy]acetyl]amino] benzoic acid, which is readily soluble in water, to provide stable pharmaceutical compositions. In particular, the invention provides a compound of the formula:

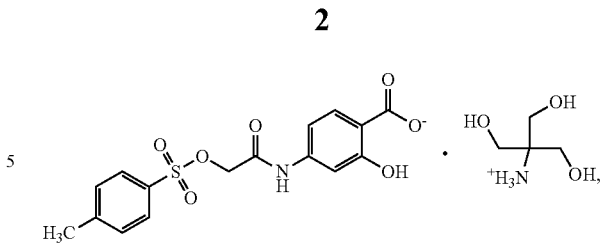

which is designated as "Compound 1" herein.

The invention further provides a pharmaceutical composition comprising Compound 1 and a pharmaceutically acceptable carrier.

Also provided are cancer treatment methods, including preventing and treating cancer with a pharmaceutical composition comprising Compound 1.

DETAILED DESCRIPTION OF THE INVENTION

Figure 1A:
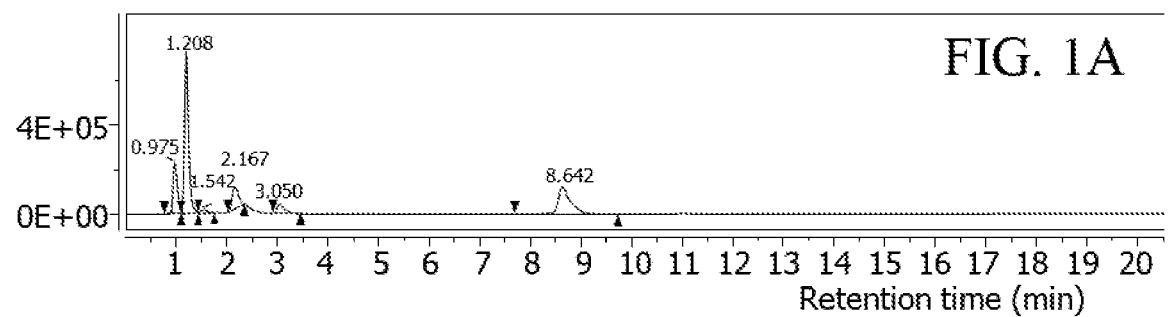
FIG. 1 is a series of high performance liquid chromatography (HPLC) chromatograms that illustrate the stability of 2-hydroxy-4-[[2-[[(4-methylphenyl)sulfonyl]oxy]acetyl]amino] benzoic acid in the presence of either LiOH (FIG. 1A), NaOH (FIG. 1B), $K_2CO_3$ (FIG. 1C), or 2-amino-2-(hydroxymethyl)-1,3-propanediol (FIG. 1D) in water. Under the conditions used to generate the data, 2-hydroxy-4-[[2-[[(4-methylphenyl)sulfonyl]oxy]acetyl]amino] benzoic acid elutes at 8.6 minutes.
Figure 1B:
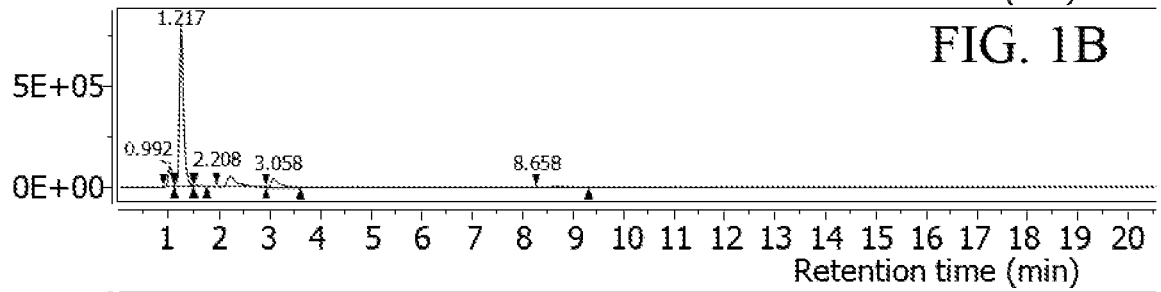
Figure 1C:
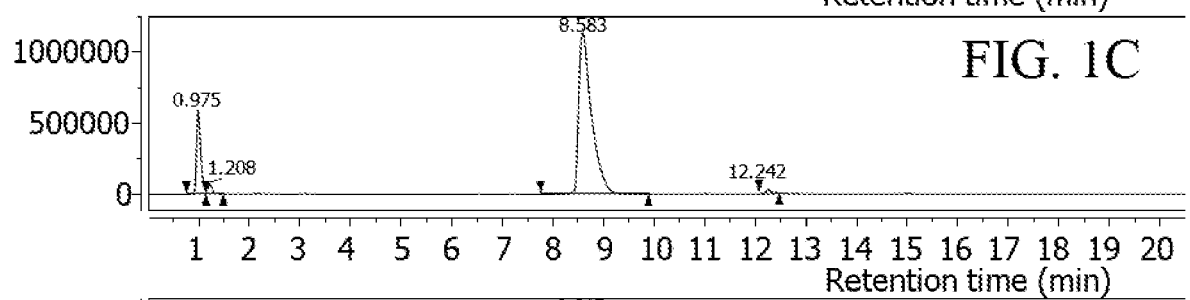
Figure 1D:
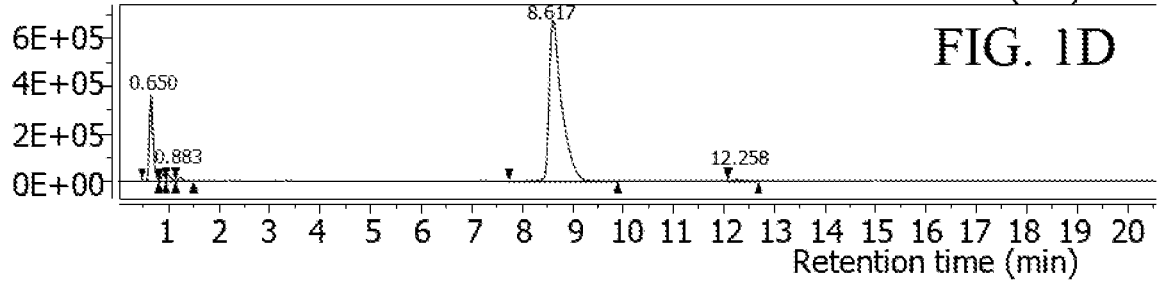

The invention provides a compound of the formula

Compound 1

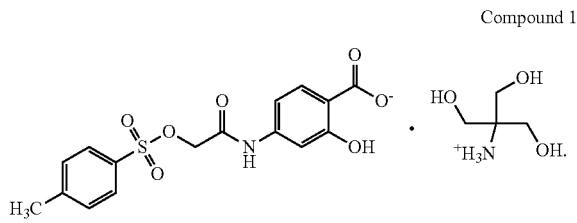 [SMILES: Cc1ccc(S(=O)(=O)OCC(=O)Nc2ccc(C(=O)[O-])c(O)c2)cc1 ; [NH3+]C(CO)(CO)CO]

Compound 1 is a salt of 2-hydroxy-4-[[2-[[(4-methylphenyl)sulfonyl]oxy]acetyl]amino] benzoic acid with 2-amino-2-(hydroxymethyl)-1,3-propanediol that was surprisingly discovered to be highly soluble in water and able to provide a clear formulation with improved stability.

U.S. Pat. No. 7,960,434 broadly describes salts of 2-hydroxy-4-[[2-[[(4-methylphenyl)sulfonyl]oxy]acetyl]amino] benzoic acid. However, U.S. Pat. No. 7,960,434 does not disclose or suggest preparing a salt from 2-amino-2-(hydroxymethyl)-1,3-propanediol.

Compound 1 can be amorphous, crystalline, or semi-crystalline. As used herein, the term "crystalline" refers to a material with an ordered structure and has a sharp melting point and that remains solid under increasing temperature until the melting point, at which point a low viscosity liquid is formed. The term "amorphous" refers to a material that has a random structure (e.g., no repeating array), whereas "semi-crystalline" refers to a material that has a combination of both crystalline and amorphous parts. In certain embodiments, Compound 1 is crystalline.

To be highly effective in a treatment method, Compound 1 should be used in as pure a form as possible. Purification techniques are known in the art and include, for example, crystallization, extraction, filtration, chromatography, distillation, and sublimation. The purity of Compound 1 can be tested by measuring, for example, the melting point. Typically, Compound 1 is at least 85% pure (e.g., at least 90% pure, at least 92% pure, at least 95% pure, at least 96% pure, at least 97% pure, at least 98% pure, or at least 99% pure). In certain aspects of the invention, Compound 1 is at least 98% pure.

The base compound, 2-hydroxy-4-[[2-[[(4-methylphenyl)sulfonyl]oxy]acetyl]amino] benzoic acid, can be purchased commercially or prepared using routine chemical procedures. See, for example, the synthesis set forth in Scheme 1 of U.S. Pat. No. 7,960,434, the disclosure of which is incorporated by reference.

2-Amino-2-(hydroxymethyl)-1,3-propanediol is commercially available and is known as, e.g., TRIZMA™ or Tris base (Sigma-Aldrich, St. Louis, Mo.).

The methods described herein comprise administering Compound 1 in the form of a pharmaceutical composition. In particular, a pharmaceutical composition comprises an effective amount of Compound 1 and a pharmaceutically acceptable carrier. The pharmaceutically acceptable excipients described herein, for example, vehicles, adjuvants, carriers, or diluents, are well-known to those who are skilled in the art and are readily available. Typically, the pharmaceutically acceptable carrier is one that is chemically inert to the active compound(s) and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously. Preferably, the pharmaceutical composition is an oral formulation.

In accordance with any of the embodiments, Compound 1 can be administered orally to a subject in need thereof. Formulations suitable for oral administration can consist of (a) liquid solutions, such as an effective amount of the compound dissolved in diluents, such as water, saline, or orange juice and can include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels.

Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. In some embodiments, the pharmaceutically acceptable carrier comprises ethanol, water, or a combination of ethanol and water. Preferably, the pharmaceutically acceptable carrier comprises water. In certain aspects, the pharmaceutical composition is a clear solution (e.g., a clear aqueous solution).

Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compound 1 can be administered in a physiologically acceptable diluent in a pharmaceutical carrier, such as a sterile liquid or mixture of liquids, including water, saline, aqueous dextrose and related sugar solutions, an alcohol (e.g., ethanol, isopropanol, or hexadecyl alcohol), glycols (e.g., propylene glycol or polyethylene glycol), glycerol ketals (e.g., 2,2-dimethyl-1,3-dioxolane-4-methanol), ethers (e.g., poly(ethyleneglycol) 400), an oil, a fatty acid, a fatty acid ester or glyceride, or an acetylated fatty acid glyceride, with or without the addition of a pharmaceutically acceptable surfactant (e.g., a soap or a detergent), suspending agent (e.g., pectin, carbomers, methylcellulose, hydroxypropylmethylcellulose, or carboxymethylcellulose), or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

Parenteral formulations will typically contain from about 0.5 to about 25% by weight of Compound 1 in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier (e.g., water) for injections, immediately prior to use. Extemporaneous injection solutions and suspensions can be prepared from sterile powders, granules, and tablets of the kind previously described.

The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions, and gels. Topical administration includes application to the oral mucosa, which includes the oral cavity, oral epithelium, palate, gingival, and the nasal mucosa. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as an anti-irritant, buffers, alcohols, glycerin, and mineral oils with various emulsifiers or dispersing agents as known in the art to obtain the desired pH, consistency, and viscosity. It is possible that the composition can be produced as a solid, such as a powder or granules. The solids can be applied directly or dissolved in water or a biocompatible solvent prior to use to form a solution that is substantially neutral (e.g., about pH 7) or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin, and silicone based materials.

In an embodiment, the solubility of Compound 1 in the pharmaceutical composition (e.g., aqueous solution), including the carrier and any other excipients present, is at least 5 mg/mL, at least 10 mg/mL, at least 20 mg/mL, at least 30 mg/mL, at least 40 mg/mL, or at least 50 mg/mL. In particular, the solubility will be about 40 mg/mL, about 45 mg/mL, about 50 mg/mL, about 55 mg/mL, about 60 mg/mL, or about 65 mg/mL.

A pharmaceutical composition comprising Compound 1, such as an aqueous solution comprising Compound 1, typically is stable (e.g., at room temperature and/or at a temperature less than room temperature) for at least 1 hour (e.g., at least 2 hours, at least 3 hours, at least 4 hours, at least 5 hours, at least 6 hours, at least 12 hours, at least 18 hours, at least 24 hours, at least 36 hours, at least 2 days, at least 2.5 days, at least 3 days, at least 3.5 days, at least 4 days, at least 4.5 days, at least 5 days, at least 5.5 days, at least 6 days, at least 6.5 days, or at least 7 days (1 week)).

To help increase the long term stability, the pharmaceutical composition can, if desired, be stored at a temperature less than room temperature, including storing the composition at 20° C. or less, 15° C. or less, 12° C. or less, 10° C. or less, 8° C. or less, 5° C. or less, 2° C. or less, or 0° C. or less. The lower limit of the temperature can be, for example, −40° C. or more, −30° C. or more, −20° C. or more, −10° C. or more, or 0° C. or more. Any two of the foregoing endpoints can be used to define a close-ended range, or can be used singly to define an open-ended range. In certain aspects of the invention, the pharmaceutical composition is a clear solution comprising water as the carrier. Preferably such composition is stored at a temperature less than room temperature (e.g., −30° C. to 0° C., about 0° C., or about −20° C.).

The pharmaceutical composition can have any suitable pH for a desired formulation and/or treatment. Typically, the pharmaceutical composition has a pH of about 7, such as a pH of about 6-8 (e.g., between 6.0 to 8.0, between 6.5 to 7.5, between 6.6 to 7.4, and between 6.7 to 7.3).

The dose administered to the subject (e.g., a mammal, such as a human) in accordance with the present invention should be sufficient to affect the desired response. A person skilled in the art will recognize that dosage will depend upon a variety of factors, including the age, condition or disease state, predisposition to disease, genetic defect or defects, and body weight of the subject. The size of the dose will also be determined by the route, timing and frequency of administration as well as the existence, nature, and extent of any adverse side-effects that might accompany the administration of Compound 1 and the desired effect. It will be appreciated by a person of skill in the art that various conditions or disease states may require prolonged treatment involving multiple administrations.

The inventive methods comprise administering an effective amount of Compound 1. An "effective amount" means an amount sufficient to show a meaningful benefit in an individual, e.g., promoting at least one aspect of tumor cell cytotoxicity (e.g., inhibition of growth, decreased cell proliferation, inhibiting survival of a cancer cell, inducing apoptosis, reducing proliferation, reducing size and/or mass of a tumor (e.g., solid tumor)), or treatment, healing, prevention, delay of onset, reducing the risk, halting, or amelioration of other relevant medical condition(s) associated with a particular cancer. The meaningful benefit observed in the subject can be to any suitable degree (10% or more, 20% or more, 30% or more, 40% or more, 50% or more, 60% or more, 70% or more, 80% or more, 90% or more, or 95% or more). In some aspects, one or more symptoms of the cancer are prevented, reduced, delayed, halted, and/or eliminated subsequent to administration of Compound 1, thereby effectively preventing and/or treating the cancer to at least some degree. In a particular embodiment, cancer cell growth is prevented, the appearance of cancer cells is delayed, the number of cancer cells is reduced, and/or cancer cells are shrunk and/or killed upon administration of Compound 1 to a subject.

Effective amounts can vary depending upon the biological effect desired in the subject and condition to be treated. In this respect, any suitable dose of Compound 1 can be administered to the subject (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of Compound 1 desirably ranges from about 0.1 mg per kilogram (kg) of the body weight of the mammal (mg/kg) (e.g., from about 0.5 mg/kg, from about 0.75 mg/kg, from about, from about 1 mg/kg, from about 2 mg/kg, from about 3 mg/kg, from about 5 mg/kg, from about 10 mg/kg, from about 20 mg/kg, from about 30 mg/kg, from about 40 mg/kg, from about 50 mg/kg, from about 60 mg/kg, from about 75 mg/kg, from about 90 mg/kg, from about 100 mg/kg, from about 125 mg/kg, from about 150 mg/kg, from about 175 mg/kg, from about 200 mg/kg, from about 225 mg/kg, from about 250 mg/kg, from about 275 mg/kg, from about 300 mg/kg, from about 325 mg/kg, from about 350 mg/kg, from about 375 mg/kg, from about 400 mg/kg) to about 800 mg/kg (e.g., to about 425 mg/kg, to about 450 mg/kg, to about 475 mg/kg, to about 500 mg/kg, to about 525 mg/kg, to about 550 mg/kg, to about 575 mg/kg, to about 600 mg/kg, to about 625 mg/kg, to about 650 mg/kg, to about 675 mg/kg, to about 700 mg/kg, to about 725 mg/kg, to about 750 mg/kg, or to about 775 mg/kg). Any two of the foregoing endpoints can be used to define a close-ended range or can be used singly to define an open-ended range. For example, the dose of Compound 1 desirably ranges from about 100 mg/kg/day to about 600 mg/kg/day, from about 125 mg/kg/day to about 500 mg/kg/day, from about 200 mg/kg/day to about 550 mg/kg/day, from about 250 mg/kg/day to about 500 mg/kg/day, about 250 mg/kg/day, or about 500 mg/kg/day.

Constitutive STAT3 activity is a marker for many types of cancers and other diseases, such as diabetic nephropathy, skeletal muscle insulin resistance in type 2 diabetes, endometriosis, depression, asthma, colitis, renal fibrosis, inflammatory bowel disease, systemic lupus erythematosus (SLE), Alzheimer's disease, Huntington's disease, and autism. See, e.g., Gkouveris et al., *Journal of Cancer Therapy*, 2015; 6: 709-726, WO 2012/159107, and WO 2010/062681. With respect to cancerous cells, aberrant STAT3 is believed to promote tumor cell invasion and metastasis. See, e.g., Yue et al., *Expert Opinion Investig Drugs*, 2009; 18(1): 45-56. Thus, in some aspects of the invention, Compound 1 inhibits and/or reduces STAT3 activity in a cell, such as a cancer cell.

Inhibition of STAT3 has been described in the art as a viable treatment of cancer, typically through prevention of STAT3 phosphorylation/activation, inhibition of DNA binding, or inhibition of STAT3 dimer formation. Suppression of STAT3 activity has been shown to induce apoptosis in cancer cells. See, e.g., Gkouveris et al., *Journal of Cancer Therapy*, 2015; 6: 709-726. Thus, Compound 1 can be administered to a subject in need thereof as part of a treatment method for cancer. In particular, the invention provides a method of preventing cancer (e.g., breast cancer) in a subject comprising administering to the subject an effective amount of Compound 1. In such a method, typically there is a delay in the appearance of cancer or cancer cells do not form, particularly in a subject at risk for a particular cancer. Further provided is a method of treating cancer (e.g., breast cancer) in a subject comprising administering to the subject an effective amount of Compound 1. In such a method, cancer cells are killed, shrunk, inhibited, and/or reduced in number.

The type of cancer to be treated or prevented is not particularly limited, but in certain aspects, the cancer is characterized as having increased STAT3 activity and/or increased Ki67 expression relative to normal tissue of the same type. See, for example, Garcia et al., *Cell Growth Differ*, 1997; 8(12): 1267-1276; Watson et al., *Br J Cancer*, 1995; 71(4): 840-844; Huang et al., *Gynecol Oncol*, 2000; 79(1): 67-73; Dhir et al., *Prostate*, 2002; 51(4): 241-246; Mora et al., *Cancer Res*, 2002; 62(22): 6659-6666; Corvinus et al., *Neoplasia*, 2005; 7(6): 545-555; Guo et al., *Am J Transl Res*, 2009; 1(3): 283-290; Schaefer et al., *Oncogene*, 2002; 21(13): 2058-2065; and Wei et al., *Oncogene*, 2003; 22(3): 319-329. For example, STAT3 is constitutively active in over 40% of all breast cancers, particularly in triple-negative breast cancers, which lack the expression of the estrogen receptor (ER), progesterone receptor (PR), and human epidermal growth factor receptor 2 (HER2/Neu) (Banerjee et al., *Int J Cancer*, 2016; 138(11): 2570-2578). Activated STAT3 has also been shown to induce estrogen biosynthesis and the subsequent proliferation of ER-positive breast epithelial cells (Ishii et al., *Cancer Res*, 2008; 68(3): 852-860), and is thought to play a role in the maintenance of tumor recurrence-promoting stem cell-like breast cancer cells and in the conversion of a non-cancer stem cell population to breast cancer stem cell-like cells (Marotta et al., *J Clin Invest*, 2011; 121(7): 2723-2735). Thus, the present STAT3 inhibitor offers a unique advantage over the FDA-approved breast cancer preventative agents tamoxifen and raloxifene in that the STAT3 inhibitor could potentially prevent multiple breast cancer subtypes. In addition, because Compound 1 as a STAT3 inhibitor has a distinct mechanism of action from the selective estrogen receptor modulators (SERMs) tamoxifen and raloxifene, such inhibitors may also be particularly useful against ER-positive breast cancers that have developed resistance to these drugs.

Examples of cancers treatable with the inventive methods include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). In some aspects, the cancer is a solid tumor.

In accordance with an embodiment, the cancer to be treated and/or prevented is selected from leukemia, multiple myeloma, pancreatic cancer, renal cancer, brain cancer, head and neck cancer, liver cancer, gastric cancer, colorectal cancer, lung cancer, breast cancer, ovarian cancer, and prostate cancer. In another embodiment, the cancer is breast cancer, ovarian cancer, prostate cancer, colorectal cancer, renal cancer, brain cancer, or pancreatic cancer. In yet another embodiment, the cancer is pancreatic cancer, liver cancer, or breast cancer. Preferably, the cancer to be treated and/or prevented is breast cancer.

The subject to be treated is in need of treatment and either has cancer, is at risk for cancer, and/or is suspected of having cancer. A subject can be at risk for cancer based on a variety of factors, including age, genetic predisposition (e.g., a family history of cancer and/or the result of a genetic screening assay), exposure to radiation, exposure to smoke, inhalation of particulates, consumption of mutagens, and/or diet. An individual with at least one first degree relative (i.e., a parent, sibling, and/or child) diagnosed with a particular cancer can suggest that the individual has a higher than average risk for that cancer. Two first degree relatives diagnosed with a particular cancer further increases the risk. Individuals can be screened and/or diagnosed for various types of cancers, including by self-exam, clinical exam, mammogram, pap test, ultrasound, digital breast tomosynthesis, biopsy, magnetic resonance imaging (MRI), x-ray, colonoscopy, blood test, urine test, rectal exam, and low-dose computed tomography (LDCT). In a particular example, a subject found to have a mutation in the breast cancer type 1 (BRCA1) gene and/or HER2 gene and/or a high expression of one or more known cancer biomarkers (e.g., Ki67, estrogen receptor, progesterone receptor, prostate-specific antigen (PSA), CA-125) typically would be recognized as an individual to be at risk for cancer (e.g., breast cancer, prostate cancer, ovarian cancer) or suspected of having cancer. In a particular example, a subject can be screened for the rate of cell growth (e.g., the proportion of cancer cells within a tumor that are growing and dividing to form new cancer cells). The levels of Ki67 can be measured, and the higher the percentage of Ki67, the more quickly cancer cells will grow. Other possible tumor markers that can be tested in a sample of a subject's blood, tissue, urine, or blood marrow include, for example, AFP, ALK gene rearrangements, B-cell immunoglobulin gene rearrangement, B2M (beta 2-microglobulin), BCR-ABL, CA 15-3, Ca-19-9, calcitonin, CEA (carcino-embryonic antigen), chromogranin A (CgA), DCP (des-gamma-carboxy, prothrombin), EGFR mutation, fibrin, fibrinogen, gastrin, hCG (human chorionic gonadotropin), JAK2 mutation, KRAS mutation, LD (lactate dehydrogenase), monoclonal immunoglobulins, SMRP (soluble mesotheline-related peptides), T-cell receptor gene rearrangement, thyroglobulin, 21-gene signature, and 70-gene signature.

Screening guidelines for assessing an individual's risk for certain cancers vary depending on the cancer. For example, breast cancer screening is recommended for (i) individuals considered to have average risk older than age 45, and (ii) testing at least annually, particularly by age 30, for individuals considered to have higher than average risk (e.g., having at least one parent, sibling, or child with breast cancer, testing positive for BRCA1, BRCA2, HER2, and/or CHEK2 gene mutation, and/or a history of chest radiation between ages 10 and 30 years). Colorectal cancer screening is recommended for individuals with average risk older than age 50 but testing can be earlier for individuals assessed with higher risk if a first degree relative has had colorectal polyps or cancer, an individual has an inflammatory bowel disease (e.g., Crohn's disease or ulcerative colitis), and/or an individual has a genetic syndrome, such as familial adenomatous polyposis (FAP) or hereditary non-polyposis colorectal cancer (Lynch syndrome). Individuals can be at risk for lung cancer if the individual has a history of heaving smoking, currently smokes or has quit within the past 15 years, and is between 55 and 80 years old. Male individuals can be at risk for prostate cancer if the individual is African American, has a first degree relative that was diagnosed with prostate cancer before age 60, and/or had a first degree relative that died from prostate cancer before age 75.

In certain embodiments of the methods described herein, Compound 1 can be co-administered with one or more (e.g., 2, 3, or more) additional anti-cancer agents (e.g., a chemotherapeutic agent) and/or radiation therapy. The terms "co-administered" or "co-administration" refer to simultaneous or sequential administration. A compound may be administered before, concurrently with, or after administration of another compound.

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof. In some preferred embodiments, a pharmaceutical composition comprises a pharmaceutically acceptable carrier, Compound 1, and either tamoxifen, raloxifene, or both tamoxifen and raloxifene.

For purposes of the present invention, the term "subject" typically is directed to a mammal. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the subject to be treated is a human. The subject can be male or female, and in some aspects of the invention, the subject is female.

The following examples further illustrate the invention but, of course, should not be construed as in any way limiting its scope.

Example 1

This example demonstrates the stability of 2-hydroxy-4-[[2-[[(4-methylphenyl)sulfonyl]oxy]acetyl]amino] benzoic acid in the presence of various bases.

Liquid chromatography-mass spectrometry (LC-MS) studies were performed, in which 1.1 molar equivalents of a variety of bases, including LiOH, NaOH, $K_2CO_3$, $NaHCO_3$, and 2-amino-2-(hydroxymethyl)-1,3-propanediol (TRIZMA™, Sigma-Aldrich, St. Louis, Mo.), were weighed, dissolved in water and added to 2-hydroxy-4-[[2-[[(4-methylphenyl)sulfonyl]oxy]acetyl]amino] benzoic acid. The resulting mixtures were examined for both solubility and stability with the results being analyzed high-performance liquid chromatography (HPLC) with UV and mass spectroscopy detection.

Figure 2:
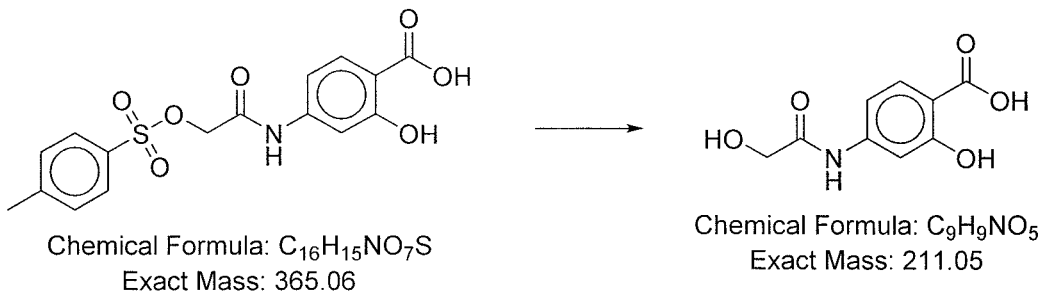
FIG. 2 is a reaction scheme illustrating the degradation of 2-hydroxy-4-[[2-[[(4-methylphenyl)sulfonyl]oxy]acetyl]amino] benzoic acid by the loss of the tosylate group.
Figure 3:
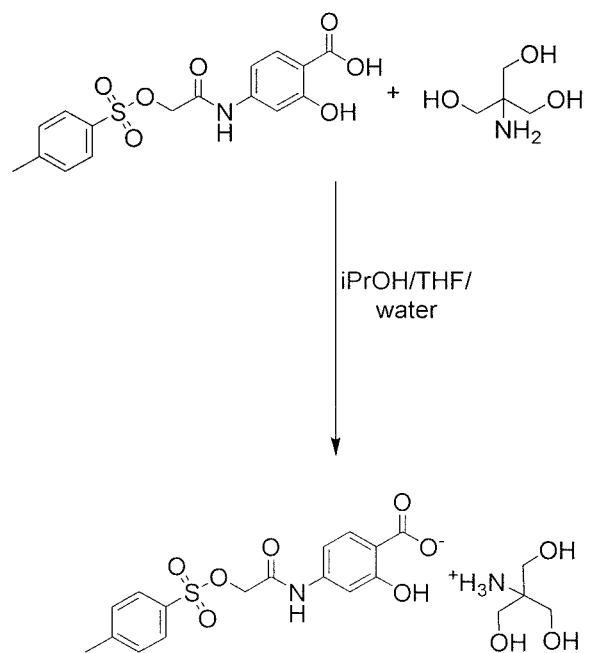
FIG. 3 is a chemical scheme illustrating a synthesis of Compound 1 in an embodiment of the invention.

For all the bases examined, 2-hydroxy-4-[[2-[[(4-methylphenyl)sulfonyl]oxy]acetyl]amino] benzoic acid exhibited good aqueous solubility, however, not every salt was stable (FIGS. 1A-1D). As seen in the mass spectra data, the primary degradant was the loss of the tosylate group (FIG. 2). Degradation was much more pronounced in stronger bases, such as sodium hydroxide. It was determined that TRIZMA™, a weaker and more hindered base, provided excellent solubility (about 60 mg/mL solubility in pH 7 water), and the product remained stable during the initial analysis (up to ~8 hours in water at room temperature).

Example 2

This example demonstrates a synthesis of Compound 1 in an embodiment of the invention.

2-Hydroxy-4-[[2-[[(4-methylphenyl)sulfonyl]oxy]acetyl]amino] benzoic acid (1.52 g, GLG-Pharma, Jupiter, Fla., lot AL650-78-4) was dissolved in 11 mL isopropanol and 18 mL tetrahydrofuran (THF). In a separate container, 506 mg 2-amino-2-(hydroxymethyl)-1,3-propanediol (TRIZMA™, Sigma-Aldrich, St. Louis, Mo., Lot SLBK9274V) was dissolved in 1.0 mL distilled water. The two mixtures were combined, mixed for 30 minutes, filtered through a 0.2 µm nylon membrane filter, and then vacuum distilled under heat. Distillation was continued until approximately one half of the volume remained, e.g., about 15 mL. Isopropanol (15 mL) was added and distillation continued until one half of the volume remained, whereupon 15 mL ethyl acetate was added, and distillation of the ternary mixture continued. Upon removal of one-half of the distillate, the ethyl acetate addition was repeated two more times, with the final distillation reducing the volume to ~5 mL to give a clear oil. Next, 5 mL isopropanol was added to give a clear solution; 25 mL ethyl acetate was then added by dropwise addition resulting in the precipitation of a white solid. The solid product was collected by filtration, and the filter cake was washed with 10 mL ethyl acetate. The isolated product was dried under vacuum to afford 1.4 g (69% yield) of a hygroscopic material.

High performance liquid chromatography (HPLC) was performed using a LC-2010CHT Liquid Chromatograph (Shimadzu, Columbia, Md.) equipped with an internal ultraviolet (UV) detector. Detection was at 261 nm. Mass spectrometry was conducted with an API4000™ triple quadrupole mass spectrometer (Sciex, Framingham, Mass.) coupled to the Shimadzu-LC. Results were acquired and processed with ANALYST™ Software, version 1.5.1 data system (Sciex, Framingham, Mass.). HPLC separation was conducted using a XSELECT™ HSS T3 C18, 75×3.0 mm, 3.5 µm column (Waters Corporation, Milford, Mass.), with a column temperature at 40° C. The mobile phase consisted of (A) 0.1% formic acid in water (LC-MS grade, Sigma-Aldrich, St. Louis, Mo.) and (B) 0.1% formic acid in acetonitrile (LC-MS grade, Sigma-Aldrich, St. Louis, Mo.). The HPLC elution program consisted of the following gradient ramp—30% B for 5 min, linear ramp to 90% B over 20 min, hold at 90% B for 5 min. This was conducted at 0.5 ml/min over 30 minutes total with a 5 minute re-equilibration period of 30% B prior to the next injection. Samples were injected at a concentration of 0.5 mg/mL with a 5 µL injection volume. Linearity was established through a standard calibration curve at concentration of 0.5, 0.25, 0.1 and 0.05 mg/mL; $r^2$=0.9997. The mass spectrometer parameters were as shown in Table 1.

TABLE 1

| Scan Type | Q1 MS |
|---|---|
| Polarity | Positive |
| Ion Source | ESI-Turbo Spray |
| Start/Stop (Da) | 100.0/600.0, Time = 0.50 sec |
| CUR | 40.0 |
| GS1 | 40.0 |
| GS2 | 40.0 |
| IS | 2500.00 |
| TEM | 500.0 |
| Ihe | ON |
| DP | 20 |
| EP | 10 |

Alternatively, HPLC was performed using an Agilent 1100 Liquid Chromatograph (Agilent Technologies, Santa Clara, Calif.) equipped with an internal ultraviolet (UV) detector. Detection was at 261 nm. Results were acquired and processed with Agilent ChemStation data system (Agilent Technologies, Santa Clara, Calif.). HPLC separation was conducted using an XBridge C18, 150×4.6 mm, 3.5 µm column (Waters Corporation, Milford, Mass.), with a column temperature at ambient temperature. The mobile phase consisted of (A) 0.1% formic acid in water (Sigma-Aldrich, St. Louis, Mo.) and (B) 0.1% formic acid in acetonitrile (Sigma-Aldrich, St. Louis, Mo.). The HPLC elution program consisted of the following gradient ramp—20% B for 5 min, linear ramp to 90% B over 20 min, hold at 90% B for 5 min. This was conducted at 0.75 ml/min over 30 minutes total with a 5 minute re-equilibration period of 20% B prior to the next injection. Samples were injected at a concentration of 0.5 mg/mL with a 5 µL injection volume.

Example 3

This example demonstrates a synthesis of Compound 1 in an embodiment of the invention.

A solution of 2-hydroxy-4-[[2-[[(4-methylphenyl)sulfonyl]oxy]acetyl]amino] benzoic acid (10 mmol) was dissolved in THF/EtOH (1:1) (250 mL), and the resulting solution was cooled to 0° C. in an ice bath. Once the solution cooled, the 2-amino-2-(hydroxymethyl)-1,3-propanediol (TRIZMA™, Sigma-Aldrich, St. Louis, Mo.) (10 mmol) was added, and the mixture was stirred for 90 minutes at 0° C. Upon completion, the solvent was removed with care taken to keep the mixture at or below room temperature. The resulting residue was triturated with pentanes, and was placed under high vacuum at 0° C. for 2 hours and then backfilled with argon. The resulting white solid (quantitative yield) was stored in the freezer (−20° C.) until ready to use.

Example 4

This example demonstrates a pharmacokinetic (PK) study of a formulation comprising Compound 1 in an embodiment of the invention.

Compound 1 (750 mg) was dissolved in 10 mL of sterile water (75 mg/mL). The resulting solution was filtered through a 0.2 µm syringe filter to provide a clear, colorless solution. This solution was then analyzed for actual concentration by HPLC against a standard. Once the concentration was determined, the solution was appropriately diluted to achieve a 50 mg/mL solution. The formulation was suitable for immediate use or for later use by storing at −20° C.

For comparative purposes, a suspension of 2-hydroxy-4-[[2-[[(4-methylphenyl)sulfonyl]oxy]acetyl]amino] benzoic acid in carboxymethylcellulose (CMC) was prepared as follows. A 0.5% solution of CMC was prepared using filtered water. A 50 mg/mL suspension was prepared by taking 500 mg of 2-hydroxy-4-[[2-[[(4-methylphenyl)sulfonyl]oxy]acetyl]amino] benzoic acid in 10 mL of the 0.5% CMC solution. The pH was adjusted to 6.0-6.5. The solution is suitable for immediate use or for later use by storing at room temperature for up to 24 hours.

Seventy female FVB-N mice, 8 to 9 weeks old and 20 to 30 g, from Charles River Laboratories (Wilmington, Mass.) were procured. Forty-eight were dosed by oral gavage (PO) with one of three dose levels of either Compound 1 or 2-hydroxy-4-[[2-[[(4-methylphenyl)sulfonyl]oxy]acetyl] amino] benzoic acid mixed with carboxymethylcellulose (CMC), eight were dosed intravenously (IV) with one dose level of Compound 1, and one was dosed by IV with placebo (see Table 2). Two mice (one in group A and one is group D) were mis-dosed, so an additional two mice were used from the extras to replace them.

TABLE 2

| PTKS Study | Dose Group | #Animals/dose | Total Animals |
|---|---|---|---|
| IV - 50 mg/kg | A | 8 | 8 |
| IV Placebo - 0 mg/kg | B | 1 | 1 |
| Compound 1 | | | |
| PO 500 mg/kg | C | 8 | 8 |
| PO 250 mg/kg | D | 8 | 8 |
| PO 125 mg/kg | E | 8 | 8 |
| CMC formulation | | | |
| PO 500 mg/kg | F | 8 | 8 |
| PO 250 mg/kg | G | 8 | 8 |
| PO 125 mg/kg | H | 8 | 8 |
| Total | | | 57 |

[a] Time points: 5, 10, 15, 30, 60, 90, 180, and 1440 min.

A dosing scheme was established as follows, however, the actual dosing amount was based on the measured weight of the mouse prior to the study. Solutions were prepared directly prior to dosing; any unused materials were stored frozen.

For 125 mg/kg dose—0.06 mL will provide 125 mg/kg for a 25 g mouse
125 mg/kg*0.025 kg mouse=3.125 mg; 3.125 mg÷50 mg/mL=0.06 mL For 250 mg/kg dose—0.125 mL will provide 250 mg/kg for a 25 g mouse
250 mg/kg*0.025 kg mouse=6.25 mg; 6.25 mg÷50 mg/mL=0.125 mL For 500 mg/kg dose—0.25 mL will provide 500 mg/kg for a 25 g mouse
500 mg/kg*0.025 kg mouse=12.5 mg; 12.5 mg÷50 mg/mL=0.250 mL Mice were weighed within 72 hours of receipt and again on Study Day −1. Mice were observed once daily prior to day 0, and at least twice daily beginning on day 0 for 24 hours post-dose for morbidity and moribundity. None of the mice in groups A-H demonstrated signs of toxicity post-dose; there was no mortality due to the oral or IV administration of Compound 1 or the CMC formulation to the mice at any of the doses administered.

Blood samples were obtained from individual mice at eight (8) time points after dose administration: 5, 10, 15, 30, 60, 90, 180, and 1440 minutes post-dose using one mouse/time point/dose group as shown above in Table 2. Animals were exsanguinated and collected blood samples were cooled for at least 3 minutes but no longer than 30 minutes, prior to centrifugation to obtain plasma for analysis. Each animal was anesthetized via $CO_2$; exsanguination was followed by pneumothorax to confirm death. All plasma samples were analyzed by UHPLC-UV-MS to determine the concentration of Compound 1, using a reverse-phase analytical method. Noncompartmental analysis (NCA) of PK data to calculate PK parameters, which included terminal half-life, AUC, bioavailability (F), Cmax and Tmax was used. The results are shown in Table 3.

TABLE 3

| Route | Parameter[a], unit | Compound 1 | CMC Formulation |
|---|---|---|---|
| IV | Dose, mg/kg | 50 | |
| | $C_{max}$, µg/ml | 3.6 | |
| | $T_{max}$, min | — | |
| | $t_{1/2}$, min | 16 | |
| | $AUC_{0-\infty}$, | 59 | |

TABLE 3-continued

| Route | Parameter[a], unit | Compound 1 | | | | CMC Formulation | |
|---|---|---|---|---|---|---|---|
| | µg/ml · min | | | | | | |
| | AUC_% Extrap, % | 1.4 | | | | | |
| | CL, mL/min/kg | 849 | | | | | |
| | $V_{ss}$, L/kg | 20 | | | | | |
| | MRT, min | 16 | | | | | |
| PO | Dose, mg/kg | 500 | 250 | 125 | 500 | 250 | 125 |
| | $C_{max}$, µg/ml | 740 | 90 | 68 | 85 | 172 | 29 |
| | $T_{max}$, min | 15 | 15 | 5 | 15 | 10 | 10 |
| | $t_{1/2}$, min | 62 | 84 | 65 | 113 | 63 | 260 |
| | $AUC_{0-\infty}$, µg/ml · min | 14 | 7.0 | 8.0 | 11 | 9.3 | 1.9 |
| | AUC_% Extrap, % | 11 | 23 | 14 | 34 | 16 | ND |
| | F, % | 2.4 | 2.4 | 5.4 | 1.9 | 3.1 | 1.3 |
| | CL, mL/min/kg | 850 | 848 | 847 | 850 | 847 | ND* |
| | MRT, min | 78 | 127 | 99 | 169 | 99 | ND |

[a]Abbreviations: $C_{max}$, maximum plasma concentration; $t_{1/2}$, terminal elimination half-life; $T_{max}$, time to reach $C_{max}$; $AUC_{0-\infty}$, area under the plasma concentration-time curve from time zero to infinite time; CL, clearance; $V_{ss}$, steady-state volume of distribution; F, oral bioavailability; MRT, mean residence time; ND, not determined.
*NCA failed to predict AUC, CL, and MRT.
$AUC_{0-3h}$ is reported here.

For the plasma stability analysis, sample preparation consisted of taking 0.1 mL of plasma, which was volumetrically pipetted into a 1.5-mL snap cap micro centrifuge tube containing 0.9 mL of acetonitrile. The tube was vortexed for ~1 min, then centrifuged at ~10,000 rpm for ~5 min. The supernatant was transferred to a HPLC vial for analysis.

A calibration curve was prepared by spiking 0.1 mL of blank plasma in a snap cap micro centrifuge tube with Compound 1 standard; generating a range of standards from 5 ng/mL to 1,000 ng/mL. The peak area response was found to be linear over the range, with a limit of detection (LOD) of 5 ng/mL (signal to noise of 3:1) and a limit of quantitation (LOQ) of 20 ng/mL.

Chromatographic separation was performed using a Waters ACQUITY™ ultra performance liquid chromatography (UPLC) equipped with UV and MS (Waters XEVO™ G2-XS Quadrupole Time of Flight (Q-TOF)) detection (Waters Corporation, Milford, Mass.). An ACQUITY™ UPLC BEH C18, 1.7 µm column was used at ambient temperature, with the autosampler set at 10° C. The mobile phase consisted of 0.1% formic acid in water (mobile phase A) and 0.1% formic acid in acetonitrile (mobile phase B), which was eluted at 0.5 mL/min for 7 min. A gradient was used starting at 90% A:10% B for 1 min then linearly increasing to 10% A:90% B over 4 min with a 1 min hold at 10:90 (A:B) for 1 min and finally a 1 min re-equilibration period at 90:10 (A:B). Injection volumes were 5 µL; UV detection was recorded at 261 nm. Mass spectral data was collected in negative electrospray ionization mode over a range of 100-800 amu, with product ion extraction performed post-data acquisition at m/z 364. The source was set at 2 kV (capillary) with a sample cone offset of 45 and a source offset of 80. The source temperature was set to 150° C. and desolvation gas and temperatures at 800 L/h and 500° C., respectively. The core gas flow was set to 20 L/h. The instrument was controlled and data collected under MASSLYNX™ software, version 4.1 (Waters Corporation, Milford, Mass.).

In order to assess the plasma stability for Compound 1, the material was taken up in mouse plasma and analyzed over time. Initially, the samples were assessed daily, but it was evident that the stability was short since no 2-hydroxy-4-[[2-[[(4-methylphenyl)sulfonyl]oxy]acetyl]amino] benzoic acid was observed after 1 day. An hour-by-hour analysis was then conducted, showing a marked decrease at ambient conditions (see Table 4). Finally, a plasma stability study at −20° C. was performed, which showed increased stability, although the increase in stability was only modest (see Table 5). It should be noted that the time measurement for ambient is listed in hours (Table 4) compared with the time for the −20° C., which was measured in days (Table 5).

TABLE 4

| Time (hours) | % Recovery* |
|---|---|
| 0 | 88.6 |
| 1 | 61.2 |
| 2 | 52.6 |
| 3 | 28.7 |
| 5 | 21.3 |
| 6 | 15.8 |

*Recovered based on comparison to a freshly prepared standard

TABLE 5

| Time (days) | % Recovery* |
|---|---|
| 0 | 94.5 |
| 1 | 76.6 |
| 2 | 65.7 |
| 3 | 58.0 |
| 6 | 46.6 |

*Recovered based on comparison to a freshly prepared standard

The stability in an acetonitrile extract (post sample preparation) was good with little/no degradation over 6 days (see Table 6). Therefore, it was desirable to extract the samples into a more stable form (acetonitrile) as quickly as possible to minimize data variation. In particular, once the centrifugation was performed on the blood samples to provide the plasma samples for analysis, extraction into acetonitrile was done as quickly as possible (e.g., <1 hour).

TABLE 6

| Time (Days) | % Recovery* |
|---|---|
| 0 | 89 |
| 2 | 89 |
| 3 | 90 |
| 6 | 90 |

*Recovered based on comparison to a freshly prepared standard

Example 5

This example demonstrates that Compound 1 inhibits Ki67 expression in normal mammary gland tissue.

Breast duct epithelium cells were contacted with a dose that was equivalent to either 500 mg/kg, 250 mg/kg, or 125 mg/mg of body weight (BW)/day of Compound 1. Cells that were not contacted with any compound served as a control. Ki67 expression was assessed by immunohistochemical analysis of the normal ductal epithelium. Stained sections were scanned and quantitated using automated image analysis software.

Figure 4:
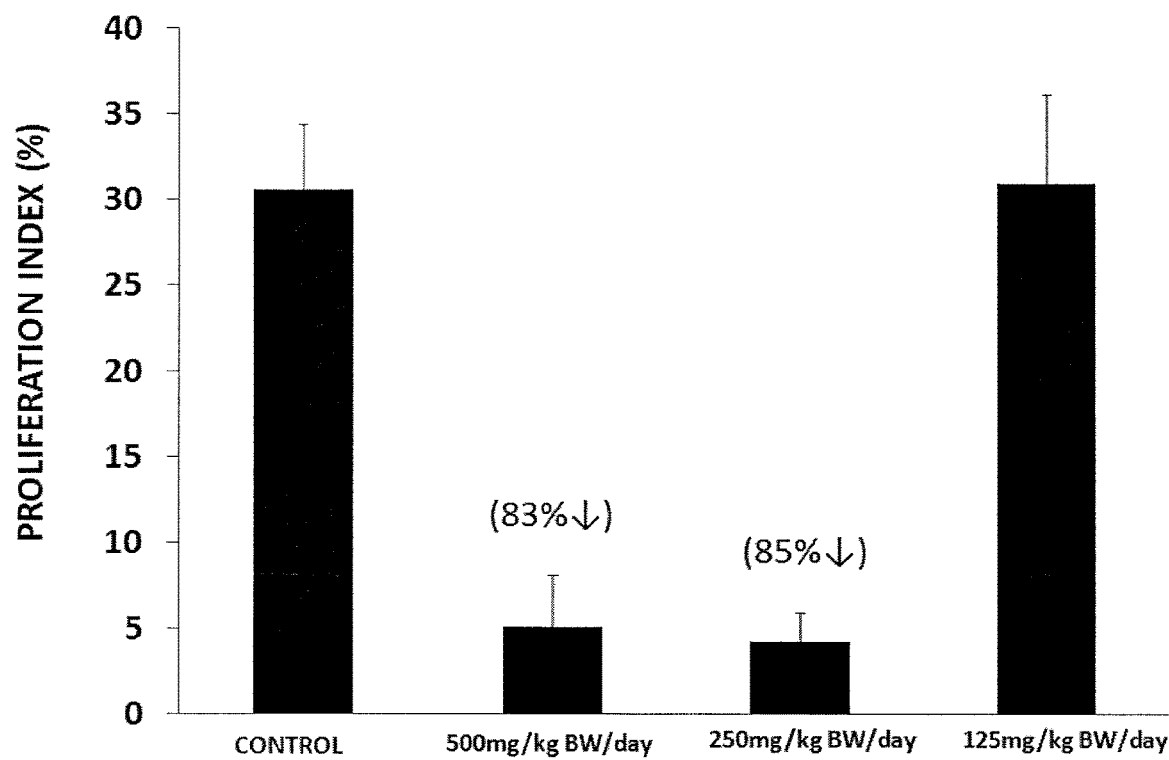
FIG. 4 is a bar graph showing the ability of an aqueous solution of Compound 1 to inhibit Ki67 expression in a normal mammary gland of female mouse mammary tumor virus (MMTV)/neu mice at various doses (500 mg/kg of body weight (BW)/day, 250 mg/kg BW/day, or 125 mg/kg BW/day) compared to a control (no administration) after two weeks of treatment.

The results are shown in FIG. 4. After two weeks of treatment, it was observed that a dose of 500 mg/kg of body weight (BW)/day of Compound 1 inhibited Ki67 by 83%, whereas a dose of 250 mg/kg BW/day of Compound 1 inhibited Ki67 by 85%. Since Ki67 is considered to be a biomarker for the development of breast cancer and other cancers, the ability to inhibit Ki67, particularly in healthy tissue, represents a viable pathway to preventing cancers, such as breast cancer.

Example 6

This example demonstrates that Compound 1 inhibits STAT3 expression in normal mammary gland tissue.

Breast duct epithelium cells were contacted with a dose that was equivalent to either 500 mg/kg, 250 mg/kg, or 125 mg/mg of body weight (BW)/day of Compound 1. Cells that were not contacted with any compound served as a control. STAT3 expression was assessed by immunohistochemical analysis of the normal ductal epithelium. Stained sections were scanned and quantitated using automated image analysis software.

Figure 5:
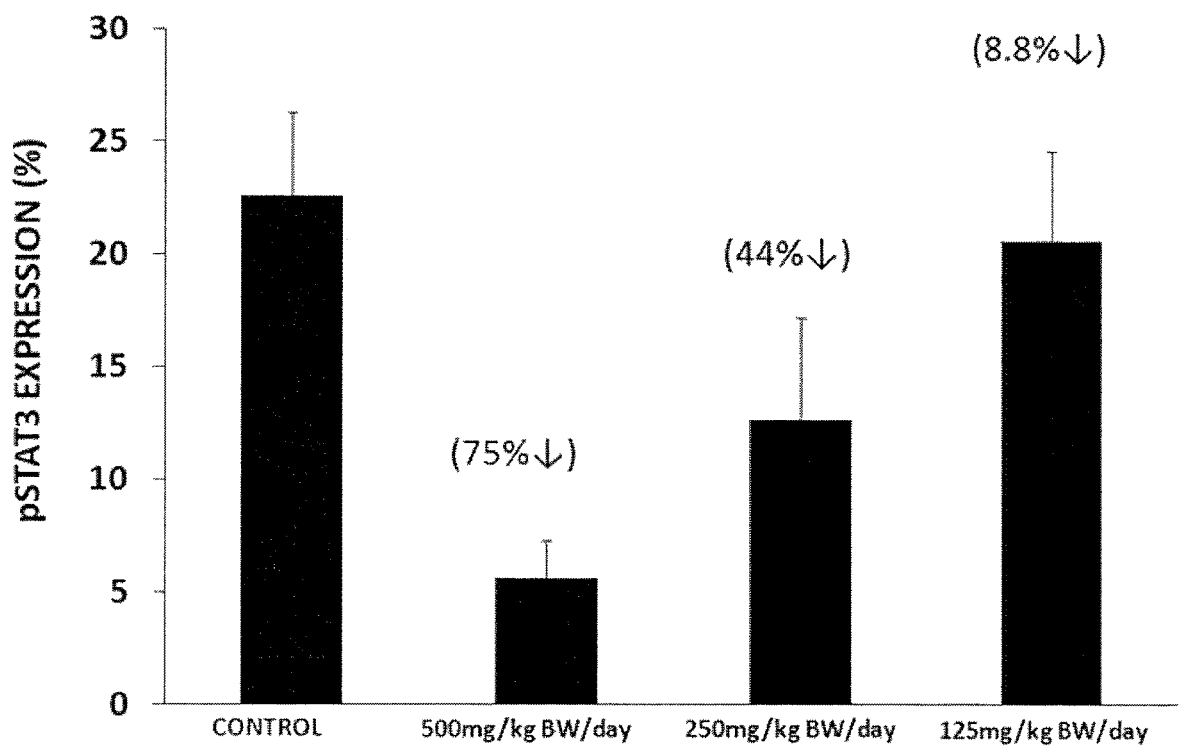
FIG. 5 is a bar graph showing the ability of an aqueous solution of Compound 1 to inhibit STAT3 expression in a normal mammary gland of female MMTV/neu mice at various doses (500 mg/kg BW/day, 250 mg/kg BW/day, or 125 mg/kg BW/day) compared to a control (no administration) after two weeks of treatment.

The results are shown in FIG. 5. After two weeks of treatment, it was observed that a dose of 500 mg/kg BW/day of Compound 1 inhibited STAT3 by 75%, a dose of 250 mg/kg BW/day of Compound 1 inhibited STAT3 by 44%, and a dose of 125 mg/kg BW/day of Compound 1 inhibited STAT3 by 8.8%. Since increased STAT3 activity is considered to be a biomarker for the development of breast cancer and other cancers, the ability to inhibit STAT3, particularly in healthy tissue, represents a viable pathway to preventing cancers, such as breast cancer.

Example 7

This example demonstrates that Compound 1 can delay the onset of breast cancer in an in vivo study.

Figure 6:
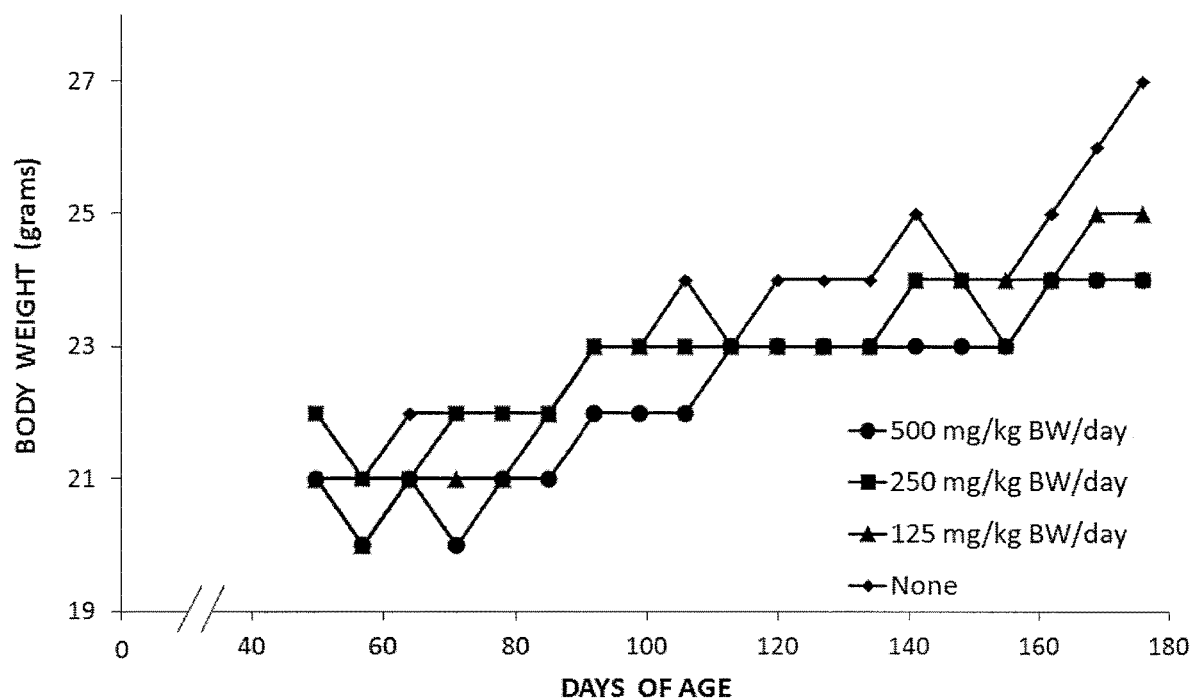
FIG. 6 is a graph demonstrating the effects of various doses of Compound 1 on body weight gain (grams) over time (days of age) of female MMTV/neu mice during a chemoprevention study. Compound 1 was administered to the mice from 50 days of age until the end of the study (4 months treatment). The administered doses were 500 mg/kg BW/day (●), 250 mg/kg BW/day (■), and 125 mg/kg BW/day (▲), relative to a control of no administered drug (♦).

Fifty-day-old female MMTV/Neu mice were administered Compound 1 by gavage 5 times/week at doses of 500, 250, and 100 mg/kg BW/day. The negative control group received vehicle (purified water) only. In order to accelerate tumor formation, the mice were also given 7,12-dimethylbenz[a]anthracene (DMBA) by gavage 1 time/week for 4 weeks beginning at 57 days of age. The study was terminated 4 months after DMBA exposure. During the treatment period, the body weights of the mice and the appearance of palpable mammary tumors were monitored on a weekly and twice-weekly basis, respectively. No weight loss or toxicity was observed in any of the groups throughout the course of the experiment (FIG. 6).

Figure 7:
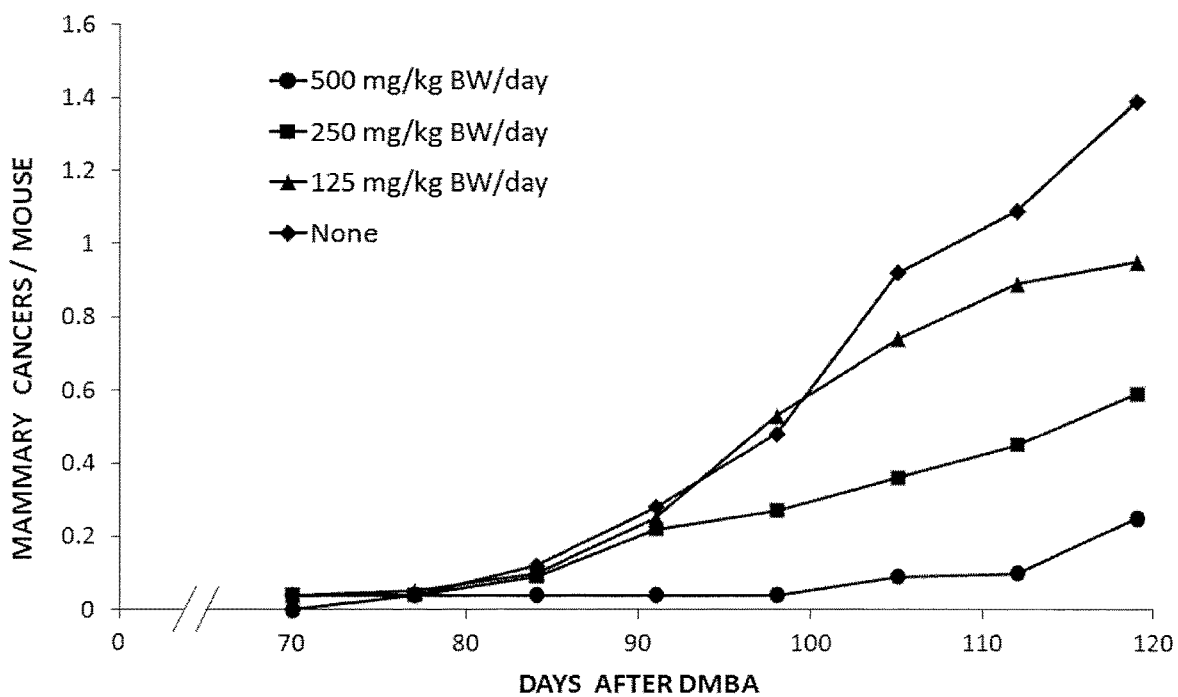
FIG. 7 is a graph demonstrating the effects of various doses of Compound 1 on the appearance of dimethylbenzanthracene (DMBA)-induced mammary cancer of female MMTV/neu mice over time (days). Compound 1 was administered to the mice from 50 days of age until the end of the study (4 months treatment). The administered doses were 500 mg/kg BW/day (●), 250 mg/kg BW/day (■), and 125 mg/kg BW/day (▲), relative to a control of no administered drug (♦).

Treatment with Compound 1 resulted in a dose-dependent decrease in the incidence, multiplicity, and weights of mammary tumors compared to the vehicle-only control (FIG. 7). At all doses tested, Compound 1 was able to delay the onset of DMBA-induced breast cancer in female mice. A dose of 500 mg/kg BW/day showed the greatest effect in preventing breast cancer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula

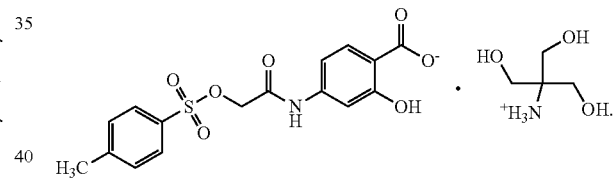

2. The compound of claim 1, wherein the compound is crystalline.

3. The compound of claim 1, wherein the compound is at least 85% pure.

4. A pharmaceutical composition comprising the compound of claim 1 and a pharmaceutically acceptable carrier.

5. The pharmaceutical composition of claim 4, wherein the pharmaceutically acceptable carrier comprises water.

6. The pharmaceutical composition of claim 4, wherein the composition is at a temperature less than 0° C.

7. The pharmaceutical composition of claim 4, wherein the composition has a pH of about 7.

8. The pharmaceutical composition of claim 4, which is a clear solution.

9. The pharmaceutical composition of claim 4, which is an oral formulation.

10. A method of preventing breast cancer in a subject comprising administering to the subject an effective amount of the compound of claim 1.

11. The method of claim 10, wherein the cancer has increased STAT3 activity and/or increased Ki67 expression relative to normal tissue of the same type.

12. A method of treating cancer in a subject comprising administering to the subject an effective amount of the compound of claim 1.

13. The method of claim 12, wherein the cancer has increased STAT3 activity and/or increased Ki67 expression relative to normal tissue of the same type.

14. The method of claim 12, wherein the cancer is selected from leukemia, multiple myeloma, pancreatic cancer, head and neck cancer, liver cancer, gastric cancer, colorectal cancer, lung cancer, breast cancer, ovarian cancer, and prostate cancer.

15. The method of claim 14, wherein the cancer is pancreatic cancer, liver cancer, or breast cancer.

16. The method of claim 15, wherein the cancer is breast cancer.

* * * * *